United States Patent [19]
Pittman, Jr. et al.

[11] 4,243,829
[45] Jan. 6, 1981

[54] PRODUCTION OF 1,7-OCTADIENE FROM BUTADIENE

[75] Inventors: Charles U. Pittman, Jr., Department of Chemistry, Box H, University of Alabama, University, Ala. 35486; Ronald Hanes, Athens, Ga.

[73] Assignee: Charles U. Pittman, Jr., University, Ala.

[21] Appl. No.: 729,465

[22] Filed: Oct. 4, 1976

[51] Int. Cl.$^3$ ............................................. C07C 11/12
[52] U.S. Cl. .................................. 585/511; 585/514; 585/601; 252/431 C
[58] Field of Search ....................... 260/680 B, 680 R; 252/431 C

[56] References Cited

U.S. PATENT DOCUMENTS

| | | | |
|---|---|---|---|
| 3,732,328 | 5/1973 | Wright | 260/680 B |
| 3,823,199 | 7/1974 | Wright | 260/680B |
| 3,970,592 | 7/1976 | Ploner | 260/680 B |

FOREIGN PATENT DOCUMENTS 1341324  12/1973  United Kingdom ................ 260/680 B

OTHER PUBLICATIONS

Gardner et al., Tetrahedron Letters 2, 163–164 (1972).

*Primary Examiner*—Delbert E. Gantz
*Assistant Examiner*—Joseph A. Boska
*Attorney, Agent, or Firm*—Oblon, Fisher, Spivak, McClelland & Maier

[57] ABSTRACT

A process for preparing 1,7-octadiene by dimerizing butadiene in the presence of a catalytic amount of palladium acetate and a tertiary phosphine, a solvent in an amount sufficient to dissolve the catalyst, a strong base and formic acid, wherein: (a) the molar ratio of the strong base to the formic acid is 1:1-2, (b) the mole ratio of tertiary phosphine to palladium is at least 1, (c) the amount of strong base present is such that the pH of the reaction medium is from 7.5 to 10.5 and (d) the solvent is at least one member selected from the group consisting of aromatic hydrocarbons, lower alkyl substituted aromatic hydrocarbons, halogenated aromatic hydrocarbons, halogenated lower aliphatic hydrocarbons, nitriles, amides, dilower alkyl ethers, lower alkyl phenyl ethers, lower alkyl esters of lower alkanoic acids, ketones and lower alkanols.

15 Claims, No Drawings

PRODUCTION OF 1,7-OCTADIENE FROM BUTADIENE

BACKGROUND OF THE INVENTION

1. Field of the Invention

The present invention relates to the production of 1,7-octadiene by hydrooligomerizing butadiene.

2. Description of the Prior Art

Linear oligimerization of butadiene is of great interest as a source of $C_8$ and $C_{12}$ unsaturated hydrocarbon intermediates useful for the synthesis of diacids, diesters, diols or diamines. Linear oligomerization of butadiene usually results in the formation of n-octatriene products, and in particular either 1,3,6-octatriene or 1,3,7-octatriene which has a terminal conjugated diene system. The desired dimer for many processes, however, is 1,7-octadiene which only has terminal double bonds. This intermediate would allow the production of products having only terminal functional groups. Butadiene dimerization products with internal double bonds would not be useful to accomplish this, since the desired terminal functional groups would not be obtained selectively in subsequent reactions. Furthermore, the conjugated system in 1,3,7-octatriene is unreactive in may reactions or gives complex reaction mixtures. Thus, a butadiene hydrooligomerization process selective to α,ω-dienes, such as 1,7-octadiens, is desired.

Wright in U.S. Pat. Nos. 3,732,326 and 3,823,199 discloses preparing either 1,6-octadiene or a mixture of 1,6 and 1,7-octadiene by dimerizing butadiene in the presence of formic acid using a palladium acetate catalyst, a phosphine and dimethylformamide, or benzene as a solvent. The yield of and selectively to 1,7-octadiene, however, are unsatisfactorily low. In addition, the catalyst efficiency is quite low.

Wright, in British Pat. No. 1,341,324, discloses dimerizing butadiene with palladium acetate in the presence of formic acid and either triethylamine or morpholine as the solvent. The product is reported to be 1,6-octadiene or a mixture of 1,6 and 1,7-octadiene. The reaction rate and selectivity to 1,7-octadiene, however, are unsatisfactory.

Gardner et al, Tetrahedron Letters No. 2, pp. 163–164, 1972, discloses essentially the same technique as Wright, except for an additional suggestion of carrying out the reaction in a basic solvent.

Roffio et al, Journal of Organometallic Chemistry, 55, 405 (1973) utilize a $(PPh_3)_2$ Pd $(C_4H_6)$ catalyst in benzene in the presence of formic acid. Roffio et al reported a 75% butadiene conversion, however, only 22% of the product was 1,7-butadiene and the major product was 1,3,7-octatriene.

Accordingly, there continues to exist a need for a process which is capable of dimerizing butadiene to 1,7-octadiene at high yields, high selectivities and good catalyst efficiency.

SUMMARY OF THE INVENTION

Accordingly, it is one object of the present invention to provide a process which dimerizes butadiene to 1,7-octadiene at a high butadiene conversion rate, high selectivity, and high catalyst efficiency.

This and other objects of the present invention, as will hereafter be better understood by the following description, have been attained by dimerizing butadiene in the presence of a system comprising palladium acetate, a tertiary phosphine, formic acid, a solvent, and a strong base wherein the molar ratio of the strong base to formic acid is 1:1-2, the molar ratio of phosphine to palladium is at least 1, and the solvent is at least one member selected from the group consisting of aromatic hydrocarbons, lower alkyl substituted aromatic hydrocarbons, halogenated aromatic hydrocarbons, halogenated lower aliphatic hydrocarbons, nitriles, amides, dilower alkyl ethers, lower alkyl phenyl ethers, lower alkyl esters of lower alkanoic acids, ketones, and lower alkanols. This is in contrast with prior art systems where a strong base was used as the solvent or no such base was present.

DETAILED DESCRIPTION OF THE PREFERRED EMBODIMENTS

Solvents suitable for use in the present invention include non-polar solvents and solvents of moderate coordinating ability. The use of a solvent which is both a strong base and a strongly coordinating solvent, such as triethylamine or pyridine, gives much lower yields and slower rates than the use of solvents of moderate coordinating ability. This may be caused by competition between the butadiene and the solvent for coordination sites at the catalyst. That is, triethylamine as the solvent would effectively compete with butadiene for palladium thereby reducing the reaction rate. Suitable solvents include aromatic hydrocarbons such as benzene, lower alkyl substituted aromatic hydrocarbons such as toluene, m-, p-, and o-xylene, halogenated aromatic hydrocarbons including chloro, bromo and iodine substituted, such as chloro benzene and the like. Halogenated lower aliphatic compounds such as chloroform, methylene chloride, carbon tetrachloride and the like may be used in particular chloroform is preferred.

Solvents of moderate coordinating ability which will function in the present invention include nitriles such as lower alkyl nitriles, hydrocarbon aromatic nitriles including acetonitrile, benzonitrile and the like, amides including benzamide, acetamide, mono- and di-substituted amides where the substituent is preferably lower alkyl. Suitable substituted amides include N-methyl acetamide, N,N dimethyl acetamide and dimethylformamide. Simple ethers such as the dilower alkyl ethers including dimethyl ether, diethylether, and the like function satisfactorily. Hydrocarbon aromatic ethers such as the lower alkyl phenyl ethers may also be used, and include methyl phenyl ether (anisole), ethyl phenyl ether (phenetole) and the like. Cyclic, saturated hydrocarbon ethers such as tetrahydrofuran, tetrahydropyran and the like are also suitable solvents. Lower alkyl diethers such as dimethoxy ethane, and the like may be used. In addition, the cyclic diethers such as 1,4-dioxane are also suitable as solvents. Simple lower alkyl esters of lower alkanoic acids such as ethyl acetate, methyl acetate, methyl butyrate and the like are also suitable solvents of moderate coordinating ability. Ketones, including lower aliphatic ketones such as methyl ethyl ketone and hydrocarbon aromatic ketones such as acetophenone are also satisfactory solvents. Lower alkanols such as isopropanol and the like may be used if desired. The preferred solvents of moderate coordinating ability include nitriles, formamides, such as dimethylformamide, dilower alkyl ethers, lower alkyl phenyl ethers, simple lower alkyl esters of lower alkanoic acids, ketones and lower alkanols.

The particularly preferred solvents include benzene, dimethylformamide, chlorobenzene, anisole, N,N-dimethylacetamide, ethyl acetate, isopropanol, benzonitrile, chloroform methyl ethyl ketone, acetonitrile, diethylether, acetophenone and toluene.

The amount of solvent added should be sufficient to maintain the palladium acetate, phosphine, formic acid, strong base and butadiene in solution. Preferably, the volume ratio of solvent to strong base is from 2:1 to 10:1, more preferably 2.5:1 to 5:1.

The strong base must be one which can neutralize formic acid according to the reaction:

$$HCOOH + B \rightarrow HCOO^- HB^+.$$

The strong base may be either insoluble or soluble in the reaction medium. While any strong base may be used, it is preferable not to use bases which will compete with the phosphine for the coordinating sites on the palladium metal. Also, the use of strong bases which cause double bond isomerization should not be used because these will lower the selectivity to 1,7-octadiene.

Also the use of bases which will react with products or which form neutralization products with formic acid which may enter into undesirable side reactions, such as hydroxide bases, should be avoided. Suitable strong bases include tertiary amines such as pyridine, triethylamine, N,N-dimethyl aniline, tributyl amine, dimethyl ethyl amine, lutidine, tripropyl amine, N-methyl morpholine, quinoline, isoquinoline and the like, as well as insoluble bases such as sodium carbonate, potassium carbonate, calcium carbonate, sodium and potassium bicarbonate, magnesium oxide, calcium and the like. The preferred insoluble bases are potassium, sodium and calcium carbonates and the potassium and sodium bicarbonates. Preferably, the strong base is soluble in the reaction medium.

The amount of strong base added is critical. The mole ratio of strong base to the formic acid must be at least equal to 1 but not exceed 2. If the ratio is less than 1, then the Pd(OAc)$_2$ is more readily reduced to palladium metal which reduces the catalyst efficiency, and which would promote the isomerization of the double bond to convert the 1,7-octadiene to 1,6-octadiene therefor lowering the selectivity. When the ratio exceeds 2, the reaction rate slows down markedly. Sufficient strong base is present to maintain the pH of the reaction medium between about 7.5 and 10.5.

The formic acid is present as a source of hydrogen for the process. Accordingly, it is desirable that some formic acid be present during the entire course of the reaction. When operating the process batch-wise, this can be accomplished by adding a stoichiometric amount of formic acid initially, 1 mole of formic acid for every 2 moles of butadiene, of by continuously or periodically adding additional amounts of formic acid. It is essential, however, that the ratio of strong base to formic acid present in the reaction medium never be less than 1 nor greater than 2.

When the process is operated continuously, the butadiene, formic acid, strong base, solvent, palladium acetate and phosphine can be charged to the reactor continuously or intermittently. Alternatively, the palladium acetate and phosphine can be bound to a solid substrate, such as a synthetic resin. This embodiment allows for the ready separation of the 1,7-octadiene product from the catalyst.

Any tertiary phosphine which can be dissolved in the reaction solvent may be used. The bisphosphines, such as 1,3-bisphenylphosphinopropane and 1,4-bisdiphenylphosphineobutane, will not function in the present invention as the tertiary phosphine, the butadiene conversions obtained are unsatisfactory. Accordingly, it is preferred to use a mono-phosphine. Suitable phosphines are represented by the formula:

$$R_1-P-R_2$$
$$|$$
$$R_3$$

wherein $R_1$, $R_2$ and $R_3$ may be the same or different and are selected from aryl such as phenyl, p-tolyl, o-tolyl, m-tolyl, p-chlorophenyl, phenoxy, p-methyl-phenoxy, p-anisoly, m-anisoyl and the like, alkyl of 1 to 8 carbon atoms, prefereably 1 to 5 carbon atoms, alkoxy having from 1 to 8 carbon atoms, but preferably from 1 to 3 carbon atoms. Preferably, $R_1$, $R_2$ and $R_3$ represent aryl, alkyl, or a mixture thereof. The more preferred tertiary phosphines, are the triaryl and trialkyl phosphines. The most preferred tertiary phosphines are the trimethyl-, triethyl-, tributyl- and triphenyl phosphines.

The mole ratio of phosphine to palladium should be at least 1. When the ratio of phosphine to palladium is at least 1, the maximum selectivity to 1,7-octadiene is obtained. The ratio of P/Pd can exceed 1, however, an excess of phosphorous has little effect on the selectivity to 1,7-octadiene. Since it is possible that dissolved oxygen may slowly oxidize phosphines to their corresponding phosphine oxides, the presence of some excess phosphine will increase the life of the catalyst system. However, the reaction can be performed in the presence of oxygen without any loss of selectivity or conversion. The ratio of phosphorus to palladium should not be too great because at large ratios, the butadiene conversion is reduced. Accordingly, it is preferred to add sufficient phosphine, so as to attain a mole ratio of phosphine to palladium of from about 1 to about 20. Still more preferably from 2:1 to 5:1.

The palladium acetate that is used in the present process is soluble in benzene. Benzene insoluble components which are catalytically inactive, as are often present in commercial sources of palladium acetate, may be converted, at least partially, into benzene soluble palladium acetate by refluxing with glacial acetic acid. This method is similar to that described by Wilkinson et al in the Journal of the Chemical Society (1965), page 3632. The palladium acetate is present in the reaction mixture in catalytic amounts; preferably, from about 0.015 to 0.7 wt.%, still more preferably from 0.05 to 0.1 wt.% of palladium acetate is present based on the total weight of the reaction medium.

Alternatively, the palladium acetate and tertiary phosphine may be bound onto a cross-linked synthetic resin instead of being dissolved in the reaction medium. Acceptable cross-linked synthetic resins include cross-linked polystyrene, poly (alpha-alkyl) acrylates, polycarbonates, polyamides and the like.

The bound tertiary phosphine may have the general formula:

$$(R_6)_m(R_6)_n$$
$$|$$
$$R_1-P-R_2$$

wherein $R_1$ and $R_2$ are as defined previously, and $R_6$ represents the repeating unit of the synthetic resin and where m is a positive integer, n is 0 or a positive integer, m+n equal the total number of repeating units in resin and the percentage of the repeating units substituted with the tertiary phosphine is represented by the formula:

$$\frac{m}{m+n} \times 100\%$$

The number of repeating units substituted with the tertiary phosphine is not critical. When less than 5% of the repeating units contain a phosphine substituent, large quantities of the resin must be used to form the bound catalyst. Accordingly, it is desirable to have at least 10% of the repeating units substituted with a tertiary phosphine. It is preferred, however, that from 20 to 40% of the repeating units contain a phosphine substituent. The substituent can be introduced into the resin using well-known techniques, such as those described by Smith et al in the Journal of the American Chemical Society, 97 (7) 1749 (1975) and by Pittman et al in Ann. N.Y. Academy of Sciences, 239, 76 (1974). In accordance with those techniques, the palladium acetate is complexed with the phosphine-substituted resin by admixing in a solvent for the palladium acetate.

Whether a soluble or a bound phosphine-palladium acetate catalyst is used, it is preferable to prepare the palladium acetate-phosphine complex before exposing the palladium acetate to formic acid. If palladium acetate and phosphine are separately added to the reaction mixture containing formic acid, an opaque brown or black solution is obtained. This is indicative of poor catalyst stability. On the other hand, a pre-complexed catalyst exhibits excellent stability, which results in high catalyst efficiencies.

The presence or absence of oxygen in the reaction has little effect on either selectivity or product yield. Thus, oxygen may be added during the reaction, but its addition affords no advantage. Should an oxygen sensitive phosphine, such as trialkyl phosphine, be used as the ligand, the presence of oxygen should be avoided.

The addition of carbon dioxide to the reaction system has been found to increase the extent of butadiene conversion, but does not affect the selectivity. When it is desired to use carbon dioxide to increase the conversion rate, the partial pressure of the $CO_2$ in the reaction system may be from about 10 to about 100 psia. Since carbon dioxide is a by-product of the process, it is possible to generate sufficient carbon dioxide in situ to enhance the conversion rates.

The reaction temperature of the process is not critical, however, it is preferred to maintain the reaction between about 40° to about 160° C. The process is conducted under a sufficient pressure to maintain liquid phase conditions at the reaction temperature.

When the method of the present invention is employed to prepare 1,7-octadiene from 1,3-butadiene the catalyst efficiencies are very high. The embodiments of the present process will convert more than 10,000 moles of butadiene for every mole of palladium acetate. If the preferred embodiments are employed, molar turnovers in excess of 14,000 are easily obtained. In the most preferred aspect of the present invention, molar turnovers in excess of 30,000 can be obtained using a constant flow continuous process with a fixed-bed catalyst arrangement. In contrast, previous processes obtained molar turnovers of only about 1,000–2,000.

Having generally described the invention, a more complete understanding can be obtained by reference to certain specific examples, which are included for purposes of illustration only and are not intended to be limiting unless otherwise specified.

In the following experiments, dry, $N_2$-saturated solvents were used in all cases. Benzene was continually refluxed over $CaH_2$ in a $N_2$ atmosphere and distilled immediately prior to use. DMF, $Et_3N$, and pyridine were distilled from KOH in a $N_2$ atmosphere and stored over KOH under $N_2$ until used.

Infrared spectra were recorded on a Beckman IR-33 grating spectrophotometer and mass spectra on a CEC 21-104 instrument. Butadiene conversions and product distributions were determined on a Hewlett-Packard model 5710A instrument using $\frac{1}{8}'' \times 6'$ columns packed with 15% tricresyl phosphate on Chromosorb W support. Quantitative GLC data were obtained via electronic integration with a Hewlett-Packard model 3380A reporting integrator. Internal standard calibration techniques were used employing either iso-octane or n-octane as an internal standard.

EXAMPLE 1

To a thick-walled Pyrex tube was charged DMF (20 ml), formic acid (3 ml., 80 mmoles) and $Et_3N$ (11.21 ml, 80 mmoles). The resulting solution was then purged with $N_2$ for 20 minutes and a DMF solution (10 ml) containing $Pd(OAc)_2$ (0.0112 g, 0.05 mmoles) and $PPh_3$ (0.131 g, 0.5 mmoles) was added. The tube was then cooled in liquid nitrogen and butadiene (9 g., 0.17 moles) condensed in. The tube was heated with stirring at 70° C. for 3 hours. After cooling the tube to room temperature, 3.3 g of gases ($CO_2$) were vented and formic acid (3 ml, 80 mmoles) was added. Butadiene (12 g., 0.22 moles) was then condensed in and the tube heated at 65° C. for 17 hours. The tube was again cooled and 3.6 g. of gases were vented. At this point, maximum reactor volume was reached so the solution was divided into two equal portions and one portion returned to the reactor. (GLC analysis showed a 6600 molar turnover at this point). Formic acid (2 ml, 50 mmoles) and butadiene (7.6 g., 0.14 moles) were then charged to the reactor and the reactor was heated at 70° C. for 3 hours. After venting 3 g. of gases, fresh formic acid (2 ml, 50 mmoles) and butadiene (7.3 g., 0.138 moles) were charged to the tube. At this point a small amount of black precipitate was observed at the bottom of the tube. After heating at 70° C. for 16.5 hrs, 3 g. of gases were vented. GLC (internal standard) of the resulting solution showed 19.4 g of octadienes, corresponding to a molar turnover of 14,100 moles butadiene/mole Pd for this portion of catalyst.

The overall butadiene conversion for this sequence of reactions was 78% with an observed selectivity to 1,7-octadiene of 81%.

EXAMPLE 2

In this example a bound catalyst was used. Polymer-bound catalysts were prepared by coordination of $Pd(OAc)_2$ to a phosphinated polystyrene resin in a benzene suspension. The phosphinated polystyrene beads were prepared by swelling, crosslinked polystyrene beads (30 g., 0.286 moles) (Bio-Beads, 200–400 mesh, 1% divinylbenzene, Bio-Rad Laboratories) in $CCl_4$ (400 ml) in a round-bottom flask and the flask was cooled in an ice bath and totally shielded from light. Iron powder (0.5 g) was added to this slurry and vigorous stirring initiated. Bromine (3.6 ml, 0.066 moles) in 100 ml $CCl_4$ was added dropwise from an addition funnel over a period of 2 hours. The reaction mixture was allowed to warm the room temperature after bromine addition was completed. Generated HBr was allowed to escape into an aqueous NaOH trap. The slurry was stirred for 24 hours, solvent removed by filtration on a coarse glass frit funnel, and unreacted iron powder was removed with a magnet. The resin was then washed by stirring successively in one liter each: 5% aqueous sodium thiosulfate (one hour), 5% aqueous sodium carbonate (one hour), acetone (4–5 hours), benzene/methanol (9:1) (18–24 hours), and methanol (4–5 hours). The beads were then vacuum dried (25° C., 0.05 torr) for 24 hours. Bromine analysis showed 15% Br.

To a stirred THF (75 ml) suspension of lithium metal chunks (5 g, 1.4 moles) was added dropwise a THF solution (140 ml) containing chlorodiphenylphosphine (40 g, 0.223 mole) under a $N_2$ atmosphere. Formation of lithiodiphenylphosphide was indicated by the appearance of a bright red color. After stirring 18 hours, unreacted lithium was removed and the solution was added slowly to a rapidly stirred THF slurry of the brominated beads (30 g, 15% Br content, 56.25 mmoles Br.). This slurry was allowed to stir one or two days under $N_2$ (longer if high precent Br content resin used). The slurry was then hydrolyzed by adding to two liters of $N_2$-saturated acetone/water (3/1) and stirring for one hour. The beads were then filtered and washed by stirring successively in one liter each of the following $N_2$-saturated solvents: water (2 hours), acetone (2 hours), benzene/methanol (9:1) (18–24 hours), and methanol (4–5 hours). The beads were then vacuum dried (80° C., 0.05 torr) for 24 hours and analyzed for %P and %Br (Schwarzkopf Microanalytical Labs, N.Y.). The cited example analyzed for 4.34%P which corresponds to 20% of the polystyryl rings substituted with the diphenylphosphide moiety. Bromine analysis showed almost quantitative replacement of bromide (0.4%Br).

The phosphinated resin (5 g, 4.34%P, 7.0 mmoles P) was then swelled in benzene (100 ml) at room temperature and Pd(OAc)$_2$ (0.6 g, 2.7 mmoles) added. This slurry was stirred 24 hours under $N_2$. The resin was then recovered by filtration and stirred in fresh benzene (300 ml) at room temperature for 3 days to remove uncoordinated catalyst. After filtration, the resin was vacuum dried (25° C., 0.05 torr) for 48 hours. Analysis showed 3.12%P and 5.69%Pd, which corresponds to a molar P/Pd ratio of 1.9:1.

To a thick-walled Pyrex tube was charged DMF (30 ml), formic acid (3 ml, 80 mmoles) and Et$_3$N (11.2 ml, 80 mmoles). The resulting solution was then purged with nitrogen for 20 minutes and the polymer-bound Pd(OAc)$_2$ (0.2348 g., $5 \times 10^{-5}$ moles) was added. The tube was then cooled in liquid nitrogen and butadiene (9 g, 0.17 moles) condensed in. The tube was then heated at 70° C. for 3 hours. After cooling to room temperature, 3.3 g gases were vented and formic acid (3 ml, 80 mmoles) was added. Butadiene (9.2 g, 0.17 moles) was then condensed in and the tube heated at 70° C. for 3 hours. 4.7 g gases were vented, formic acid (3 ml, 80 mmoles) and butadiene (9 g, 0.17 moles) charged to the tube and the tube then heated at 70° C. for 4 hours. At this time the maximum reactor volume was reached and the catalyst was recovered by filtration on a glass frit funnel under a nitrogen cone. The catalyst was then recharged to a $N_2$-purged solution of DMF (30 ml), formic acid (3 ml, 80 mmoles) and Et$_3$N (11.2 ml, 80 mmoles). Butadiene (9 g, 0.17 moles) was condensed in the tube heated at 70° C. for 2.5 hours, at which time 3.7 g of gases were vented. Formic acid (3 ml, 80 mmoles) and butadiene (9.5 g, 0.18 moles) were recharged. After heating at 70° C. for 9.5 hours, 4.3 grams of gases were vented.

Butadiene (9 g, 0.17 moles) and formic acid (3 ml, 80 mmoles) were recharged and the tube heated at 70° C. for 3.5 hours. The solution was then filtered as before, and the catalyst replaced in a fresh DMF, Et$_3$N, formic acid (3 ml, 80 mmoles) solution. Butadiene (9 g, 0.17 moles) was condensed in and the solution heated at 70° C. for 19 hours. GLC analysis at this point showed 60% unreacted butadiene. Recharging butadiene (9 g, 0.19 moles) and formic acid (3 ml, 80 mmoles) and heating at 70° C. for 8 hours produced no further butadiene conversion, indicating that the catalyst was inactive at this point. GLC analysis indicated formation of 24.9 grams octadiene products. This corresponds to a molar turnover of 9000. Overall selectivity was observed to be 81%.

COMPARATIVE EXAMPLE 1

In order to demonstrate the criticality of the reaction system of the present invention a series of experiments were performed using a variety of systems. In these experiments, the amounts of the palladium component, phosphine (when present) solvent and formic acid set forth in Table 1 were charged into the reaction vessel. The resulting solution purged with $N_2$ for 20 minutes. The reactor was then cooled (liquid nitrogen or Dry Ice/acetone bath) and the amount of 1,3-butadiene set forth in the table was condensed into the reaction. The reactor was then warmed in tap water and placed in an oil bath at the reaction temperature. After the required reaction time, the reactor was cooled, weighed, gases vented, and the reactor reweighed. Weight losses corresponded to the expected weight of $CO_2$ generated from formic acid decomposition. Immediately following this procedure GLC analysis of the product solution was performed. The results are set forth in Table 1.

TABLE 1

CATALYST EVALUATION

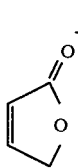

| Run No. | Catalyst (mmoles) | T° C. | Rxn. Time (hours) | % Butadiene Conversions | % Selectivity to 1,7-Octadiene |
|---|---|---|---|---|---|
| 1 | Pd(OAc)$_2$/PPh$_3$[a] (0.09) (0.2) | 100 | 24 | 63 | 73 |
| 2 | PdCl$_2$(PPh$_3$)$_2$[b] (0.014) | 95 | 24 | 50 | 62 |
| 3 | PdCl$_2$[c] (0.057) | 100 | 23 | 40 | 60 |
| 4 | (see structure) (0.1) | 100 | 24 | 16 | 50 |
| 5 | K$_2$PtCl$_4$[b] (0.024) | 100 | 54 | 25 | 3 |
| 6 | Pt(acac)$_2$/PPh$_3$[b] (0.017) (0.085) | 100 | 24 | None | — |

[a]DMF solvent, (HCO$_2$H) = 2.26M, (C$_4$H$_6$) = 8M
[b]DMF solvent, (HCO$_2$H) = 1.5M, (C$_4$H$_6$) = 6.7M
[c]DMF solvent, (HCO$_2$H) = 1.25M, (C$_4$H$_6$) = 4.3M; Pd mirror formed
[d]acetone solvent, (HCO$_2$H) = 3.65M, (C$_4$H$_6$) = 5.1M  acac = acetyl acetonate

EXAMPLE 3

A series of experiments were performed to demonstrate the criticality of using both a strong base and a solvent. The results of these eperiments are set forth in Table 2.

TABLE 2

Hydrodimerization of 1,3-Butadiene Effect of Solvent and Added Triethylamine.[a]

| Run No. | Solvent | Strong Base | Conversion % | Selectivity % 1,7-octadiene |
|---|---|---|---|---|
| 1 | Hexane[b] | Et$_3$N | 0 | — |
| 2 | Toluene[c] | — | 0 | — |
| 3 | Toluene[b] | Et$_3$N | 65 | 87 |
| 4 | Benzene[c] | — | 32 | 60 |
| 5 | Chlorobenzene[c] | — | 0 | — |
| 6 | Chlorobenzene[b] | Et$_3$N | 70 | 85 |
| 7 | Anisole[c] | — | 0 | — |
| 8 | Anisole[b] | Et$_3$N | 73 | 85 |
| 9 | Diethyl ether[c] | — | 13 | 71 |
| 10 | Diethyl ether[b] | Et$_3$N | 43 | 80 |
| 11 | Tetrahydropyran[c] | — | 77 | 75 |
| 12 | Tetrahydropyran[b] | Et$_3$N | 71 | 81 |
| 13 | Tetrahydrofuran[c] | — | 71[e] | 83 |
| 14 | Tetrahydrofuran[b] | Et$_3$N (5:1) | 56[e] | 85 |
| 15 | Tetrahydrofuran[g] | Et$_3$N | 83[d] | 83 |
| 16 | p-Dioxane[c] | — | 81 | 83 |
| 17 | p-Dioxane[b] | Et$_3$N | 64 | 86 |
| 18 | Dimethoxyethane[c] | — | 87 | 77 |
| 19 | Dimethoxyethane[b] | Et$_3$N | 62 | 81 |
| 20 | Acetonitrile[c] | — | 0 | — |
| 21 | Acetonitrile[b] | Et$_3$N | 51 | 78 |
| 22 | Benzonitrile[c] | — | 0 | — |
| 23 | Benzonitrile[b] | Et$_3$N | 63 | 85 |
| 24 | Methyl Ethyl Ketone[c] | — | 18 | 51 |
| 25 | Methyl Ethyl Ketone[b] | Et$_3$N | 72 | 82 |
| 26 | Acetophenone[c] | — | 12 | 56 |
| 27 | Acetophenone[b] | Et$_3$N | 64 | 84 |
| 28 | Acetophenone[g] | Et$_3$N | 86[d] | 85 |
| 29 | Chloroform | — | 0 | — |
| 30 | Chloroform[b] | Et$_3$N | 20 | 75 |
| 31 | Carbon Disulfide[c] | — | 0 | — |
| 32 | Carbon Disulfide[b] | Et$_3$N | 0 | — |
| 33 | Ethyl Acetate[c] | — | 19 | 70 |
| 34 | Ethyl Acetate[b] | Et$_3$N | 54 | 83 |
| 35 | Dimethyl Sulfoxide[c] | — | — | 78 |
| 36 | Isopropanol[c] | — | 45 | 66 |
| 37 | Isopropanol[b] | Et$_3$N | 75 | 68 |
| 38 | Dimethylformamide[c] | — | 82[c] | 75 |
| 39 | Dimethylformamide[f] | Et$_3$N (2.5:1) | 87 | 88 |
| 40 | Dimethylformamide[h] | Et$_3$N | 88[e] | 89 |
| 41 | Dimethylformamide[i] | Et$_3$N | 96[e] | 86 |
| 42 | Dimethylformamide[f] | Et$_3$N (2.5:1) | 96[e] | 88 |
| 43 | Dimethylformamide[f] | Et$_3$N (5:1) | 85 | 87 |
| 44 | Dimethylformamide[f] | Et$_3$N (5:1) | 74[c] | 83 |
| 45 | Dimethylformamide[g] | Et$_3$N | 85 | 84 |
| 46 | Dimethylformamide[f] | pyridine (5:1) | 96 | 84 |
| 47 | Dimethylformamide[f] | pyridine | 2[c] | 78 |
| 48 | N,N-Dimethylacetamide[c] | — | 70 | 84 |
| 49 | N,N-Dimethylacetamide[b] | Et$_3$N | 75 | 85 |
| 50 | Pyridine[c] | — | 36[c] | 78 |
| 51 | Pyridine[c] | — | 72 | 85 |
| 52 | Et$_3$N[c] | — | 40 | 86 |

[a] All reactions run at 90° for 45 min. Unless otherwise specified the P/Pd = 10. Pd(OAc)$_2$, 0.1 mmol; HCOOH, 40 mmol; 1,3-butadiene, 100 mmol. The amount of Et$_3$N was 40 mmol unless specified otherwise.
[b] 28 ml of solvent used
[c] 33.6 mol of solvent used
[d] P/Pd = 5
[e] P/Pd = 2
[f] Total volume of solvent plus base was 23 ml.
[g] Reaction run at 70° for 1.5 hr. using 54 mmol each of HCCOH and Et$_3$N, and 18.7 ml of sovlent.
[h] Reaction run at 50° for 1.5 hr. using 55 mmol each of HCOOH and Et$_3$N, 19.2 ml DMF and 120 mmol butadiene.
[i] Same as h except at 70°.

These results demonstrate some the advantages of using both a strong base and a solvent in the reaction mixture. In most of the experiments both butadiene conversion and the selectivity to 1,7-octadiene is greater than using either the solvent or the strong base alone. In addition, the Table demonstrates that some solvents, carbon disulfide, DMSO and hexane, apparently will not function as suitable solvents when a tertiary amine is used as the strong base. The conversion and selectivity values for run numbers 14 and 47 are not what was expected and may be the result of experimental error.

EXAMPLE 4

A series of experiments were conducted to demonstrate the results obtained when different phosphines are complexed with the palladium acetate. In these experiments the reaction temperature was 70° C. and the time of the reaction was 1.5 hours. The ratio of a phosphine to palladium was 2:1 and 0.1 m moles of palladium were used (added as palladium acetate.) The palladium acetate, phosphine and 0.12 moles of dimethylformamide were charged to the reactor. Then 0.05 moles of formic acid, 0.05 moles of triethyl amine were added. The resulting solution was purged with N$_2$ for 20 minutes. The reactor was then cooled (liquid nitrogen or Dry Ice/acetone bath) and 0.1 moles of 1,3-butadiene were condensed into the reactor. The reactor was then warmed in tap water and placed in an oil bath at 70° C. After 1.5 hours, the reactor was cooled, weighed, gases vented, and the reactor reweighed. Immediately following this procedure GLC analysis of the product solution was performed. The results are tabulated in Table 3.

TABLE 3

PHOSPHINE EFFECT

| Run No. | Phosphine Used | % Butadiene Conversion | % Selectivity to 1,7-Octadiene |
|---|---|---|---|
| 1 | P(OCH$_3$)$_3$ | 80 | 82 |
| 2 | PPh$_3$ | 96 | 87 |
| 3 | PBu$_3$ | 95 | 92 |
| 4 | PEt$_3$ | 95 | 93 |
| 5 | PPh$_2$—(CH$_2$)$_4$—PPh$_2$ | 24 | 83 |
| 6 | PPh$_2$—(CH$_2$)$_3$—PPh$_2$ | 28 | 90 |
| 7 | PPh$_2$—(CH$_2$)$_2$—PPh$_2$ | 0.8 | — |

The use of trialkyl phosphines gave the highest selectivity to 1,7-octadiene at very high yields. On the other hand, the bisphosphines all gave very low conversion rates of butadiene.

EXAMPLE 5

A series of experiments were conducted to demonstrate the effect varying the ratio of phosphine to palladium. The amount of phosphine necessary to achieve the ratio of phosphine to palladium set forth in Table 4 was charged into a reactor along with 0.1 m moles of palladium, 0.05 moles of formic acid, 0.05 moles of triethylamine and 0.1 moles of dimethylformamide as the solvent. The resulting solution was purged with $N_2$ for 20 minutes. The reactor was then cooled (liquid nitrogen or Dry Ice/acetone bath) and 0.1 moles of 1,3-butadiene were condensed into the reactor. The reactor was then warmed in tap water and placed in an oil bath at 90° C. After 45 minutes, the reactor was cooled, weighed, gases vented, and the reactor re-weighed. Weight losses in most cases correspond to the expected weight of $CO_2$ generated from formic acid decomposition. Immediately following this procedure GLC analysis of the product solution was performed. The results are set forth in Table 4.

TABLE 4

| | P/Pd RATIO EFFECT | | |
|---|---|---|---|
| Run No. | P/Pd | % Butadiene Conversion | % Selectivity to 1,7-Octadiene |
| 1 | 0 | 46 | 1.0[a] |
| 2 | 1 | 94 | 87 |
| 3 | 2 | 96 | 86 |
| 4 | 5 | 94 | 88 |
| 5 | 10 | 87 | 88 |
| 6 | 20 | 75 | 88 |

[a]99% 1,6 isomer obtained

The results of these experiments demonstrate that at phosphine to palladium ratios less than 1, both the butadiene conversion rate and the selectivity to 1,7-octadiene are unsatisfactory. On the other hand, run number 6 demonstrates that excessive quantities or phosphine depress the rate of butadiene conversion.

EXAMPLE 6

A series of experiments were performed to demonstrate the effect of adding either carbon dioxide or oxygen to the reaction mixture. In these experiments 0.1 m moles of palladium were charged as palladium acetate to the reactor along with triphenyl phosphine (mole ratio of $PPh_3$/Pd of 2:1), 0.05 moles of formic acid and 0.05 moles of triethylamine and 0.12 moles of dimethylformamide as the solvent. The reactor was then cooled (liquid nitrogen or Dry Ice/acetone bath) and 0.1 moles of 1,3-butadiene were condensed into the reactor. The reactor was then warmed in tap water and placed in an oil bath at 90° C. After 45 minutes, the reactor was cooled, weighed, gases vented, and the reactor re-weighed. Weight losses correspond to the expected weight of $CO_2$ generated from formic acid decomposition. Immediately following this procedure GLC analysis of the product solution was performed. In run number 1, the solution resulting after mixing the solvent, triethylamine and formic acid was purged to remove any carbon dioxide that was present. A comparision of this run with run number 2, where 25 psig of $CO_2$ was charged, shows that the butadiene conversion increased while selectivity remained essentially unchanged.

In run number 3, oxygen was excluded by using a nitrogen purge and three freeze-thaw cycles. A comparison of this run with run number 4 where 25 psig of oxygen was added during the reaction reveals that both butadiene conversion and the selectivity remained essentially unchanged.

TABLE 5

| | $O_2$—$CO_2$ EFFECTS ON REACTION | | |
|---|---|---|---|
| Run No. | | % Butadiene Conversion | % Selectivity to 1,7-Octadiene |
| 1 | $N_2$-purge | 73 | 88 |
| 2 | 25psig $CO_2$ | 98 | 85 |
| 3 | Freeze-thaw | 92 | 87 |
| 4 | 25psig $O_2$ | 91 | 86 |

EXAMPLE 7

In this experiment, the bound catalyst as prepared in Example 2 is compared with the homogeneous catalyst system. The results are set forth in Table 6.

TABLE 6

CATALYSIS OF BUTADIENE HYDRODIMERIZATION WITH POLYMER-ANCHORED PALLADIUM ACETATE[a]

| Catalyst | P/Pd | Temp. °C. | Time hr | % Conversion | % Selectivity to 1,7-Octadiene |
|---|---|---|---|---|---|
| Resin A[b] | 1.9 | 70 | 1.5 | 81 | 87 |
| Resin B[b] | 7.1 | 70 | 1.5 | 86 | 86 |
| Pd(OAc)$_2$/PPh$_3$ | 2 | 70 | 1.5 | 96 | 87 |
| Pd(OAc)$_2$/PPh$_3$ | 5 | 70 | 1.5 | 85 | 84 |
| Resin B | 7.1 | 90 | .75 | 74 | 84 |
| Pd(OAc)$_2$/PPh$_3$ | 10 | 90 | .75 | 87 | 88 |

[a]Each reaction was run in DMF/Et$_3$N (2.5:1) with 0.1 mmol Pd, 50 mmol HCOOH, 50 mmol Et$_3$N, 120 mmol DMF, and 100mmol butadiene.
[b]Resin A and B were 1% divinylbenzene-cross-linked polystyrene polymers, derivatized with diphenylphosphine groups, in the form of beads with a particle size of 200–400 mesh. Resin A had 20% of its phenyl rings derivatized with phosphine groups while Resin B had 40% of its phenyl rings derivatized.

These results demonstrate that the selectivity of the polymer bound catalysts is almost identical to the selectivities obtained with the homogeneous catalyst systems. Increasing the density of the phosphine groups in the resin from 20 to 40% substitution did not change the selectivity. The reactions catalyzed by resins A or B were somewhat slower than those catalyzed by the homogeneous systems at comparable P/Pd ratios. The lower reactivity may be due to diffusion effects or increased competition for the metal coordination sites by the matrix bound phosphine.

Having now fully described the invention, it will be apparent to one of ordinary skill in the art that many changes and modifications can be made thereto without departing from the spirit or scope of the invention as set forth herein.

What is claimed as new and desired to be secured by Letters Patent is:

1. A process for preparing 1,7-octadiene which comprises dimerizing butadiene in the presence of a catalytic amount of palladium acetate and a tertiary phosphine, a tertiary amine, formic acid and a solent in an amount sufficient to maintain the catalyst, tertiary amine, formic acid and butadiene in solution wherein:

the molar ratio of the tertiary amine to the formic acid is 1:1-2;

the mole ratio of tertiary phosphine to palladium is at least 1;

the amount of tertiary amines present is such that the pH of the reaction medium is from about 7.5 to 10.5; and the solvent is at least one member selected from the group consisting of aromatic hydrocarbons, lower alkyl substituted aromatic hydrocarbons, halogenated aromatic hydrocarbons, halogenated lower aliphatic hydrocarbons, nitriles, amides, dilower alkyl ethers, lower alkyl phenyl ethers, cyclic ethers, diethers, lower alkyl esters or lower alkanoic acids, ketones, and lower alkanols.

2. The process of claim 1, wherein the tertiary phosphine has the formula:

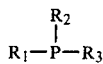

wherein $R_1$, $R_2$ and $R_3$ are the same or different and are selected from the group consisting of aryl, alkyl of 1 to 8 carbon atoms and alkoxy of 1 to 8 carbon atoms.

3. The process of claim 1, wherein the mole ratio of formic acid to butadiene is about 1:2.

4. The process of claim 2, wherein $R_1$, $R_2$ and $R_3$ are all the same and are selected from the group consisting of aryl and alkyl of 1 to 8 carbon atoms.

5. The process of claim 1, wherein the tertiary amine is at least one member of the group consisting pyridine, triethylamine, tributylamine, N-methylmorpholine, lutidine, N,N-dimethylaniline, benzyldimethyl amine, tripropylamine, quinoline, and isoquinoline.

6. The process of claim 1, wherein the solvent is dimethylformamide and the strong base is triethylamine or pyridine.

7. The process of claim 1, wherein sufficient solvent is present to dissolve all the palladium acetate and tertiary phosphine.

8. The process of claim 1, wherein the mole ratio of tertiary phosphine to palladium acetate does not exceed 20:1.

9. The process of claim 1, wherein the palladium acetate and tertiary phosphine are complexed prior to being added to the reaction system.

10. The process of claim 1, wherein the palladium acetate and tertiary phosphine are complexed in the reaction system before the addition of the formic acid or butadiene.

11. The process of claim 1, wherein the solvent is at least one member selected from the group consisting of benzene, dimethylformamide, chlorobenzene, anisole, N,N dimethylacetamide, ethyl acetate, isopropanol, benzonitrile, chloroform, methyl ethyl ketone, acetonitrile, diethylether, acetophenone and toluene.

12. The process of claim 1, wherein the volume ratio of solvent to tertiary amine is from 2:1 to 10:1.

13. A reaction medium for the conversion of butadiene to 1,7-octadiene which comprises a catalytic quantity of palladium acetate, a tertiary phosphine, a tertiary amine, formic acid and a solvent in an amount sufficient to maintain said palladium acetate, tertiary phosphine, tertiary amine, butadiene and formic acid in solution, wherein:

the molar ratio of tertiary amine to formic acid is 1:1-2;

the mole ratio of tertiary phosphine to palladium is at least 1;

the amount of artiary-amine is such that the pH of the reaction medium is from 7.5 to 10.5; and the solvent is at least one member selected from the group consisting of aromatic hydrocarbons, lower alkyl substituted aromatic hydrocarbons, halogenated aromatic hydrocarbons, halogenated lower aliphatic hydrocarbons, nitriles, amides, dilower alkyl ethers, lower alkyl phenyl ethers, cyclic ethers, diethers, lower alkyl esters of lower alkanoic acids, ketones and lower alkanols.

14. The reaction medium of claim 13, wherein the tertiary phosphine has the formula:

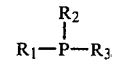

wherein $R_1$, $R_2$ and $R_3$ are the same or different and are selected from the group consisting of aryl, alkyl of 1 to 8 carbon atoms and alkoxy of 1 to 8 carbon atoms.

15. The reaction medium of claim 13, wherein the solvent is dimethylformamide and the tertiary amine is triethylamine or pyridine.

* * * * *